(12) United States Patent
Hua et al.

US008975380B2

(10) Patent No.: US 8,975,380 B2
(45) Date of Patent: Mar. 10, 2015

(54) ANNEXIN V VARIANT AND ITS PREPARATION AND APPLICATION

(75) Inventors: Zichun Hua, Jiangsu (CN); Minjin Hu, Jiangsu (CN)

(73) Assignee: Targetpharma Laboratories (Changzhou) Co., Ltd., Changzhou (CN)

( * ) Notice: Subject to any disclaimer, the term of this patent is extended or adjusted under 35 U.S.C. 154(b) by 0 days.

(21) Appl. No.: 13/505,454

(22) PCT Filed: Aug. 29, 2011

(86) PCT No.: PCT/CN2011/001449
§ 371 (c)(1),
(2), (4) Date: Jan. 6, 2014

(87) PCT Pub. No.: WO2012/126157
PCT Pub. Date: Sep. 27, 2012

(65) Prior Publication Data
US 2014/0127736 A1    May 8, 2014

(30) Foreign Application Priority Data

Mar. 24, 2011  (CN) .......................... 2011 1 0072451

(51) Int. Cl.
*C07K 16/00*       (2006.01)
*A61K 38/00*      (2006.01)
*C07K 14/47*      (2006.01)
*A61K 51/08*      (2006.01)
*G01N 33/68*      (2006.01)
*A61K 49/00*      (2006.01)

(52) U.S. Cl.
CPC ........... *C07K 14/4747* (2013.01); *A61K 51/087* (2013.01); *C07K 14/4721* (2013.01); *G01N 33/6872* (2013.01); *C07K 2319/00* (2013.01); *A61K 49/0056* (2013.01)
USPC ................... 530/388.15; 514/70.14

(58) Field of Classification Search
None
See application file for complete search history.

(56) References Cited

U.S. PATENT DOCUMENTS 6,962,903 B2 * 11/2005 Allison ........................ 514/14.9

* cited by examiner

*Primary Examiner* — James H Alstrum Acevedo
*Assistant Examiner* — Jeanette Lieb
(74) *Attorney, Agent, or Firm* — Elie Gendloff; TechLaw, LLP

(57) ABSTRACT

The invention provides the design, preparation methods and applications of the variant of annexin V. The variant of annexin V is the protein with amino acid residue sequence in sequence 1 in the SEQUENCE LISTING, characterized in that it is the protein derived from sequence 1 by one or several amino acid residues of the sequence 1 being substituted, missing or being added and its amino acid residues have the same activity with the sequence of the sequence 1. The variant protein of the annexin V prepared form the preparation methods of the variant of the annexin V has high purity, high productivity, high labeling efficiency and stability, without effect to the biological function of the variant of the annexin V, which is applicable to industrial production and allows for further research of the variant of the annexin V.

7 Claims, 2 Drawing Sheets

ANNEXIN V VARIANT AND ITS PREPARATION AND APPLICATION

CROSS REFERENCE TO RELATED APPLICATIONS

This application is a 371 of International Application No. PCT/CN2011/00144, filed Aug. 29, 2011, which claims priority to Chinese Patent Application No. 201110072451.2, filed Mar. 24, 2011, which applications are hereby incorporated herein by reference in their entireties and from which applications priority is hereby claimed under 35 U.S.C. §119 (e) and §120.

FIELD OF THE INVENTION

The invention relates generally to gene engineering and biotechnology, and more specifically to variants of annexin V, the preparation of variants of annexin V, and their pharmaceutical applications.

BACKGROUND OF THE INVENTION

Annexin V belongs to the annexin family, which is a group of proteins that are highly conserved evolutionarily, and which has the property of binding with $Ca^{2+}$ and phosphate esters. They are structurally homologous and are considered to be the membrane-bound elements regulated by $Ca^{2+}$. The same function of annexin family is: in the presence of $Ca^{2+}$, high affinity for acidic phosphate ester molecules. The annexin family is found in the higher and lower eukaryotes. The annexin members exist in many diverse types of cells, and their biochemical effects are closely related with immune properties, such as playing a role in the anticoagulation, and anti-inflammatory process, especially in the cell replication, differentiation and exocytosis process (Iwasaki A, Suda M, Nakao H, et al, Biochem., 1987, 10: 1261; Pollard H B, Haigler H T, Biol Chem, 1990, 265: 21207). The biological function of the members of the family also need further study. Although people still do not understand very well the function in vivo of the members, however, it is thought generally that the binding activity of the annexin with phosphate is the base of annexin family's activity in vitro, and relates to their physiological properties.

At present, the main applications of annexin V are the detection of apoptosis. Apoptosis, which is also known as programmed cell death (PCD), is an important part in the cell life cycle, and is a gene-regulated initiative dead process of cells different from the process of necrosis and accidental death. Cell's apoptosis is an important way to adjust and maintain the relative balance of the organism; and is also closely related to a variety of disease pathology. In the process of development of tumors and radiotherapy and chemotherapy, cerebral and myocardial ischemia reperfusion injury and the rejection in organ transplant, the cell's apoptosis and change can be found. The cell's apoptosis is a process of programmed cell death in which cells actively participate in, involving a series of change of biological molecules and cell morphology; wherein, when the apoptosis occurs, phosphatidylserine (PS) will be flipped and exposed to the outside of the cell membrane (Fadok V A, Voelker D R, Campbell, P A, Cohen J J, Bratton D L, Henson P M, J Immunol, 1992, 148(7): 2207-2216). It is an early event in apoptosis occurring before the morphological changes of the apoptotic cells (Narula J, Strauss H W, 2003, J Nucl Med, 44(3):397-399), and it is also the initial event of apoptotic cascade reaction. As a sign of the reorganization of the apoptotic cells by phagocytes, it further lead to the shrinkage of the cytoplasm, the concentration of chromatin and the degradation of the nuclear DNA etc. Therefore, the flipped PS is the most studied and most promising and most possible application foreground detection target for the apoptosis, which can early detect the apoptosis with high timeliness, (Bold R J, Termuhlen P M, McConkey D J, Surg Oncol, 1997, 6(3):133-142). At home and abroad, it is regular to use of drugs combinations with PS-specific to detect the apoptosis.

Because of its specific affinity for (P S Meers P, Mealy T. Biochemistry, 1993, 32(43): 11711-11721) the annexin V specifically binds to the surface of a cell which is in the apoptotic process, so that, the annexin V can be used for the detection of apoptotic cells after labeled by fluorescent protein or radioactive material. This method is widely used in the research of the cell and molecular biology and immunology (Koopman G, Reutelingsperger C, Kuijten G A, et al. Blood, 1994, 84(5):1415-1420; Vermes I, Haanen C, SteVens-Nakken H, et al. J Immunol Methods, 1995, 184(1): 39-510; Zhang G, Gurtu V, Kain S R, et al. Biotechniques, 1997, 23(3): 525-531; Vriens P W, Blankenberg F G, Stoot J H, et al. J Thorac Cardiovasc Surg, 1998, 116(5): 844-853; Boldt A, Barten M J, Weiss C, et al. Cytometry A, 2006, 69(3): 158-160). The annexin V labeled by fluorescein (such as FITC, PE, etc.) or biotin was used as a probe to check the phenomenon of apoptosis through the flow cytometry or fluorescence microscopy, and that is a sensitive, efficient and mature laboratory method for detection. But the clinical specimens, in addition to blood, need be detected by tissue biopsy with traumatic, and during the operation the apoptosis is easily caused and the results of the analysis are affected. Therefore, the detection in vivo of apoptosis needs to explore new methods. For example, the apoptosis imaging in vivo with annexin V labeled by radionuclide, achieves the noninvasive apoptosis imaging of the cell in vivo, to monitor the apoptosis in vivo in real time. This type of apoptosis imaging has made great progress in the areas of monitoring cell's apoptosis in vivo. At present, the applications of the recombinant annexin V labeled with radioactive material in the assessment of ischemic injury, the allograft rejection response and the evaluation of the tumor-treatment of the chemotherapeutic drugs are still in the trial of clinical experiment (Watanabe H, Murata Y, Miura M, et al. Nucl Med Commun, 2006, 27(1): 81-89; Blankenberg F G, Kalinyak J, Liu L, et al. Eur J Nucl Med Mol Imaging, 2006, 14: 1-9).

Although the labeling of the protein of polypeptide by radioactive iodine (*I) is simple, mature, and can retain their original biological activity, but the supply of $^{123}I$ and $^{124}I$ fitted the imaging in vivo is difficult. The most reported is the annexin V labeled with 99mTc. The advantage of 99mTc is its half-life of 6 hours, so that a timely imaging can be obtained, and also dose to patient is less, and it can be easily obtained from Mo/Tc generator. However, the labeling of the annexin V directly by 99mTc is difficult, and the labeling rate is low, and during the labeling process there will be some denatured protein which affect its distribution of radioactivity in the body being generated (Takei T, Kuge Y, Zhao S, et al. J Nucl Med, 2004, 45(12): 2083-2087). Therefore, the labeling of the annexin V by 99mTc is based on the principle of indirectly labeling. The bifunctional chelating agents commonly used include N-1-imino-4-mercaptobutyl (Imino) (Kemerink G J, Liem I H, Hofstra L, et al. J Nucl Med, 2001, 42(2): 382-387), ethylenediamine cysteine (EC) (Yang D J, Azhdarinia A, Wu P, et al. Cancer Biother Radiopharm, 2001, 16(1):73-83), disulfur dinitride ($N_2S_2$, also known as BTAP) (Kemerink G J, Boersma H H, Thimister P W, et al. Eur J Nucl Med, 2001, 28(9):1373-1378) etc., and the most common is hydrazinonicotinyl (HYNIC), that has been clinically trialed (Penn D L, Kim C, Zhang K, et al. Nucl Med Biol, 37(1): 29-34; Rottey S, Slegers G, Van Belle S, et al. J Nucl Med, 2006, 47(11): 1813-1818; Kartachova M, Haas R L, Olmos R A, et al. Radiother Oncol, 2004, 72(3): 333-339; Kemerink G J, Liu X, Kieffer D, et al. J Nucl Med, 2003, 44(6): 947-952). Biological behaviors in vivo of the labeled products prepared by different bifunctional chelating agents has a greater difference, wherein the labeled-products prepared by 99mTc with Imino have a higher intake in the liver, kidney and spleen, and have a relatively long biological half-life in vivo; the labeled-products prepared by $N_2S_2$(BTAP) have a higher intake in the liver, kidney, spleen and inferior belly; the labeled-products prepared by HYNIC are metabolized through kidney instead of intestinal tract, so that they have a higher intake in the kidney and liver and have a long have a relatively long biological half-life in vivo (Boersma H H, Kietselaer B L, Stolk L M, et al. J Nucl Med, 2005, 46(12): 2035-2050). In addition, the indirectly labeling method is complex, and the product need being purified, and it is not easily to be made into a kit, so their clinical use is subject to certain restrictions.

The recent studies reveal that: during the genetic recombinant expression of the annexin V, after the structural modification, it becomes very profitable for the labeling directly by 99mTc, for example, Zhang Lina etc. added 10 histidines in the N-terminus of the annexin V protein (Zhang L N, Yang X, Hua Z C, Preparative Biochemistry and Biotechnology, 2000, 30(4): 305-312). A good expression the annexin V protein in which 10 histidines are added is obtained, and it has high activity for the detection of apoptosis in vivo and vitro (Zhang L N, Yang X, Hua Z C, Preparative Biochemistry and Biotechnology, 2000, 30(4): 305-312; Ye F, Fang W, Wang F, et al. Nuclear Medicine and Biology, doi: 10.1016/j.nucmedbio.2010.11.002; Zheng Yumin, Wang Zizheng, Yan Jue, etc. Journal of Chinese nuclear medicine, 2008, 28(6): 378-382; Song Liping, Hua Zichun, Zhang Xin, etc. Journal of China clinic medical imaging, 2010, 21(1): 53-55; Song Liping, Hua Zichun, Zhang Xin, etc. Journal of China clinic medical imaging, 2010, 21(5): 358-360). Tait J F, etc. added 7 amino acids in the N-terminus, including 1-2 cysteine residues, to get three mutants, separately named as: annexin V-116, annexin V-117 and annexin V-118 (Tait J F, Brown D S, Gibson D F, et al. Bioconjug Chem, 2000, 11(6): 918-925; Tait J F, Smith C, Gibson D F, Bioconjug Chem, 2002, 13(5): 1119-1123). Their binding activitis with membrane are consistent with the natural annexin V, and have similar biological distributions with the 99mTc-HYNIC-annexin V (Tai J F, Brown B S, U.S. Pat. No. 7,204,972 B2). The three variants of the annexin V can express in the cytoplasm of the E. coli, and can be isolated and purified, with the product yield of 10 mg/L (Tait J F, Brown D S, Gibson D F, et al. Bioconjug Chem, 2000, 11(6): 918-925; Tait J F, Smith C, Gibson D F, Bioconjug Chem, 2002, 13(5): 1119-1123; Tai J F, Brown B S, U.S. Pat. No. 7,204,972 B2). However, the application of the recombinant annexin V has the following questions:

Currently, recombinant annexin V labeled with radioactive material has the disadvantages of low labeling efficiency. Meanwhile, due to the low labeling rate and the generation of some denatured proteins occurring during the labeling, the radioactive distribution of the annexin V in vivo will be affected. In clinically trials, it is also found that the annexin V is mainly distributed in kidney, liver and spleen (Rottey S, Van den Bossche B, Slegers G, Van Belle S, van de Wiele C, Q. J. Nucl. Med. Mol. Imaging, 2009, 53(2): 127-32).

Because of the low yield, the preparation method of the recombinant annexin V does not meet the needs of practical application. Due to the recombinant annexin V commonly is the form of inclusion body when express in E. coli, so the foreign scholars researched the recombinant annexin V expressed by the yeast to solve the problem of easy formation of inclusion bodies in E. coli. Even in the latest research and patents of the international authority on annexin V, American professor Tait J F and his research group, three kinds of recombinant annexin V variant, in which N-terminus seven amino acids are added, are expressed in the in E. coli and purified, its productivity is only 10 mg/L, and the needs of the practical application is meet unsuccessfully. The purification process including ultrasonication, cell membrane adsorption and dissociation, Mono Q ion exchange chromatography (elution concentration: 0.22 M NaCl), ultrafiltration and dialysis. The inventor of the present invention built an annexin V in which 10 histidines are added in the preliminary studies 10 years ago, and the labeling efficiency significantly increased and method is simple, but the final productivity was only 7.4 mg/L (Zhang L N, Yang X, Hua Z C, Preparative Biochemistry and Biotechnology, 2000, 30(4): 305-312). The expression level and yield is similar to the yield of the three recombinant variants of the annexin Vin which N-terminus seven amino acids are added by American professor Tait J F and his research group, that indicate that: there is a exist serious bottleneck in the production of recombinant annexin V.

SUMMARY OF THE INVENTION

In order to overcome the problem of the two aspects exist in the production and labeling of the annexin V protein and its variant, the purpose of the present invention is to provide a variant of the annexin V and its preparation method with high level and mass production, and its application of the preparation of detection probe for cell's apoptosis in vitro and in vivo or diagnostic drugs.

In order to achieve the above purpose, the invention is implemented by the following technical scheme: a variant of the annexin V, which is the protein that has the amino acid residue sequence in sequence 1 in the SEQUENCE LISTING; or the protein derived from sequence 1 by one or several amino acid residues in sequence 1 being substituted, missing or being added, and which has the same activity with amino acid residues in sequence 1.

The above-mentioned variant of the annexin V, wherein, a short peptide with flexible structure, and without the branched chain of amino acid is added into the C-terminus of annexin V, wherein the short peptide has 1-25 amino acid residues, mainly composed by the amino acids without branched chain such as, glycine, alanine, serine etc., and contains 1-3 cysteines.

The above mentioned variant of the annexin V can be obtained by adding one cysteine into the C-terminus of the annexin V.

A preparation method of the above-mentioned variant of the annexin V, may be carried out by the following steps:
on the basis of the crystal structure of the annexin V, molecular modeling and design of the amino acid sequence for being added to the C-terminus of the annexin V is carried out, with the help of the computer-aided molecular design;
designing a pair of primers of the encoding sequence of the annexin V, conducting the PCR amplification with human annexin V gene maintained in our laboratory as a template;

connecting the recycled product of the PCR electrophoresis to the cloning vector and transferring it into the competent *Escherichia coli* cell Top10, and conducting culture;

the recycled product of step c and the expression vector pET28a are digested separately by restriction enzymes of Nco I and Xho I, and the two obtained objective gene fragments are connected by T4 DNA ligase, and transferring it into the competent *Escherichia coli* cell Top10 and conducting the culture, and screening to extract the recombinant expression plasmid;

transferring the extracted recombinant expression plasmid into the expression host bacteria of *Escherichia coli*, BL21 (DE3), culturing the strain to get the bacteria liquid, inducing the bacteria liquid with IPTG, collecting strain;

expanded culturing the strain obtained in step e, collecting the bacteria;

crushing, cracking, purifying the bacteria, to collect the purified protein.

In the above preparation method of the variant of the annexin V, the nucleotide sequences of the pair of primers are:

```
the sense primer:
5'-gtt cca tgg gcg cac agg ttc tca gag gca-3';

the anti-sense primer:
5'-tcc gct cga gtt agc agt cat ctt ctc cac aga
gca-3'.
```

In the above preparation methods of the variant of the annexin V, the purifying step in step g contains successively precipitation desorption, ammonium sulfate fractional precipitation, the column chromatography by Super Q-650M and the column chromatography by SP.

The above preparation method of the variant of the annexin V as detection probe for cell's apoptosis is conducting fluorescent chemical label or radionuclide label.

The application of the above-mentioned variant of the annexin V as the detection probe for cell's apoptosis is the application of the preparation of monitoring reagent of cell's apoptosis, monitoring drug of disease.

The preparation method comprises adding a short peptide with 1-25 amino acid residues containing one or more cysteines to the C-terminus of the annexin V, through the use of computer-aided molecular design and the construction of the annexin V variant; obtaining the gene of the designed variant of the annexin V; constructing recombinant plasmid; the corresponding recombinant genetic engineering expression; and the separating, purifying, obtaining step of the variant of the annexin V. Wherein, the productivity of the variant of the annexin V is much higher than the productivity of the reported annexin V and its variant.

The application of the variant of the annexin V in the preparation of detection probe for cell's apoptosis in vitro and in vivo or diagnostic drugs disclosed in the present invention is further conducted through the following technical solutions: easily labeling the variant of the annexin V obtained with fluorescent chemicals or radionuclide, to be used in the preparation of the detection probe for apoptosis in vitro and in vivo or diagnostic drugs.

In the computer-aided molecular design of the variant of the annexin V, we determine the length of the amino acids to be added into the C-terminus of the annexin V, through conducting the molecular modeling and molecular design of amino acids to be added into the C-terminus of the annexin V with using structural modeling and molecular design o annexin V variant, on the basis of the crystal structure of annexin V. The purpose of adding cysteine residues to the C-terminus of the annexin V is improving the labeling efficiency of the recombinant annexin V, by using the characteristics that cysteine residues are easy to participate in the coupling reaction and have affinity for metal ions etc. The results showed that: in the short peptide length extent of 25 amino acids calculated during the computer molecular design, as long as the short peptide comprise by the amino acid residues, which does not containing branched chain and have a greater flexible, such as: glycine, alanine, serine, etc., and wherein the contained cysteine number is not more than three, there will not be any impact on the structure of the annexin V. And in the short peptide length extent of 25 amino acids calculated by molecular dynamics, which does not containing branched chain and have a greater flexible, the length of the short peptides is larger, the disturbance to the structure of the annexin V is smaller. Relatively, when the length is smaller, it may have a certain impact to the protein structure of the annexin V, which may lead to impact the function of the annexin V as an apoptosis probe for recognizing the apoptotic cells. And although adding cysteines can help for conducting labeling with fluorescein or radionuclide, but the results of molecular design show that: the number of cysteines should be controlled in the range of 1-3, if not, the polymerization of the protein will likely occur.

On the basis of the above molecular design, we first selected the design program with only a cysteine residue being added to the C-terminus of the annexin V, because the computer simulation shows: this program has the greatest impact to the chemical label (with fluorescein or radionuclide) of the annexin V, or after the chemically labeling with fluorescein/radionuclide, has the greatest possibility to impact the structure of the annexin V and the function of identify apoptotic cells. In other design programs, there all be a distance from molecules surface of the annexin V, so the interference and influence is much smaller.

We also try to express the variant of the annexin V, in which C-terminus of the short peptide containing alanine-glycine-glycine-serine-serine-glycine-glycine-cysteine, and the variant of the annexin V variant of 25 amino acid residues containing the above 3 repeating glycine-(alanine-glycine-glycine-serine-serine-glycine-glycine-cysteine)$_3$, and the similar results are obtained. Thus, it confirms the correctness of the computer molecular design. In contrast, the expression level of the variant of the annexin V only one cysteine added is highest, the expression levels of other variants are slightly lower, but all more than 60 mg/L.

In the genetic expression method of the variant of the annexin V, the PCR reaction conditions are: pre-denaturation at 94° C. for 5 minutes, then undergo the 30 cycles of amplification as denaturation at 94° C. for 30 seconds, anneal at 58° C. for 30 seconds, polymerization at 72° C. for 30 seconds, finally polymerization for 7 minutes at 72° C., then preservation at 4° C.

Furthermore, in the expression method of the variant of the annexin V, after the recombinant expression plasmid was transformed into the host strain of *E. coli* BL21 (DE3), the monoclonal product is took to shaking culture overnight at 37° C., then is inoculated in LB culture solution in condition of the volume ratio of 1:100, and culturing at 37° C. for 2 hours until OD$_{600}$ is approximately 0.6. adding the inducer IPTG to the bacteria liquid until the final concentration is 0.5 mM, inducing expression at 37° C. for 4 hours. The bacteria is collected and analyzed by 12% SDS-PAGE. The expression level and the productivity of the variant of the annexin V in the range of 10-40° C. do not significantly change.

Furthermore, the variant of the annexin V generated bacteria in the above step, and the bacteria obtained is resuspended with the proportion of 5 mL buffer (50 mM $NH_4Cl$, pH 9.0) to 1 g wet bacteria. Adding lysozyme to treat the bacterial, adding the sucrose until concentration is 60% after 1 hour, then being diluted by the buffer (50 mM $NH_4Cl$, 20 mM $CaCl_2$, pH 9.0) with 20 times volume, centrifuging and removing the supernatant, and retaining the precipitation. Resuspending the precipitate with the proportion of 5 mL desorption solution (50 mM $NH_4Cl$, pH 9.0, 20 mM EDTA) to 1 g precipitate, centrifuging and acquiring the supernatant Ammonium sulfate graded precipitating of the supernatant obtained above, collecting the 40%-70% parts of the precipitation. After the precipitation is dissolved again and dialyzed, filtrating to remove insoluble matter. Then conducting Super Q-650M chromatography, using initial buffer (50 mM $NH_4Cl$, pH 9.0) to balance the Super Q-650M chromatography column (Japan TOSOH company), eluting with elution buffer (50 mM $NH_4Cl$, pH 9.0, 200 mM NaCl), collecting elution peak. Conducing SP chromatography to the elution peak, using initial buffer (20 mM $NH_4Cl$, 80 mM NaCl, 15 mM $CaCl_2$, pH 9.0) to balance SP chromatography column, eluting with elution buffer (20 mM $NH_4Cl$, 400 mM NaCl, pH 9.0), collecting elution peak. The above separation and purification methods can make the productivity up to 110 mg/L, with its purity more than 97%.

In the purification process, the experimental results show that, when the purifying by SP column chromatography, as opposed to the annexin V, the combination of the variant of the annexin V with the SP column is more firmly, so it will be eluted unless the ionic strength is higher. This illustrates, from another perspective, that: the binding capacity with the metal ion of the variant of the annexin V is stronger than the one of the annexin V. The combination of the variant of the annexin V with more calcium ions causes the more solid combination of the annexin V variant with SP column. This verifies the effectiveness of the variant of the annexin V designed by us, form another perspective.

Furthermore, the variant of the annexin V is fluorescent chemically labeled or radionuclide labeled. The labeled variant of the annexin V can be used for monitoring the cell's apoptosis in vitro and in vivo.

We labeled the annexin V and the variant of the annexin V separately by the fluorescein FITC, to the following use to monitor the cell's apoptosis. The results show that: both the FITC-variant of the annexin V (FIG. 3A) and FITC-annexin V (FIG. 3B) can identify apoptotic cells, and has a dose-dependent relationship. But compared with the FITC-annexin V, the same dosage of the FITC-variant of the annexin V has a stronger signal, which indicates that the efficiency of the variant of the annexin V labeled by FITC is higher; and a stronger fluorescence signal is engendered when the number of the probe molecules is equal.

We labeled the $^{99m}$Tc-annexin V and $^{99m}$Tc-variant of the annexin V with radionuclide respectively, repeating the labeling of every protein three times. The labeling efficiency of the variant of the annexin V is very steady, and the labeling efficiency of the annexin V changes greatly, so the variant of the annexin V is easier to be labeled. In addition, after the $^{99m}$Tc-annexin V stilled for 3 hours, the specific radioactivity is 95%, after 24 hours, the specific radioactivity is 65%; however, after the $^{99m}$Tc-variant of the annexin V stilled for 3 hours, the specific radioactivity is 98%, after 24 hours, the specific radioactivity is also more than 90%. Therefore, the variant of the annexin V labeled by radionuclide has favorite stability. The $^{99m}$Tc-annexin V and $^{99m}$Tc-variant of the annexin V labeled with radionuclide were injected into animals. All of them exhibited the same tissue distribution and metabolic characteristics, and therefore they all can be used for monitor by imaging in vivo.

The beneficial effects of the present invention are: (1) conducting the design of C-terminus amino acid sequence, on the base of existing annexin V; by the design of the variant in which the short peptide sequence containing at least one cysteine is added, compared with the traditional method of adding the amino acid sequence into the N-terminus of annexin V, the labeling efficiency can be improved greatly without the effect to the activity of its biological function; meanwhile, using the step of advanced precipitation and desorption, ammonium sulfate grated precipitation, Super Q-650M chromatography and SP chromatography to conduct the separation and purification of proteins, and the yield of the protein is greatly increased to more than 10 times of the yield of traditional methods; (2) the protein of the variant of the Annexin V has high purity, high productivity, high labeling efficiency and stability, and without affects to the biological function of the variant of the annexin V, is applicable to industrial production, and lay the foundation for further study of the variant of the annexin V and the applications as monitoring reagents for cell's apoptosis, monitoring drugs for diseases etc.

DETAILED DESCRIPTION OF THE INVENTION

Embodiment a: structural modeling and molecular design of the variant of the annexin V: On SGI computer workstations, by using the molecular design software of MSI company (InsightII, Discover, and other modules), on the basis of the crystal structure of the annexin V, conducting molecular model and molecular design of the amino acids to be added into the C-terminus of the annexin V, to determine the length of amino acids can be added into the C-terminus. And selecting the variant of the annexin V variant with a cysteine added into the C-terminus of the annexin V as the basis for the subsequent implement steps.

Embodiment b: construction the prokaryotic expression vector of the protein of the variant of the annexin V: According to the disclosed gene sequence of annexin V, the sense primer and the anti-sense primer is designed and chemically synthesized. With the human annexin V gene preserved in the laboratory as a template, using the PCR method to amplify, the encoding DNA sequences of the variant of the annexin V is obtained, wherein, the nucleotide sequence of the primers are:

```
The sense primer:
5'- gttccatgggcgcacaggttctcagaggca-3';

The anti-sense primer:
5'-tccgctcgagttagcagtcatcttctccacagagca-3'.
```

The conditions of PCR reaction are: pre-denaturation at 94° C. for 5 minutes, then 30 cycles of amplification as denaturation at 94° C. for 30 seconds, aneal at 58° C. for 30 seconds, polymerization for 30 seconds at 72° C., and the last polymerization at 72° C. for 7 minutes, then preservation at 4° C.

Embodiment c: connecting the recycled product by PCR electrophoresis with the cloning vector and transferring it into the competent *Escherichia coli* cells Top10 to culture.

Embodiment d: the recycled product of step c and the expression vector pET28a are digested separately by restriction enzymes of Nco I and Xho I, mixing the recovered pET28a vector fragment and human DNA fragment of the variant of the annexin V by the ratio of 1:20, and connecting them by T4 DNA ligase, transforming the product into competent bacteria of *E. coli* Top10, screening the positive clones to identification by restriction and DNA sequencing analysis to verify the correctness of the encoding sequence.

Figure 1:
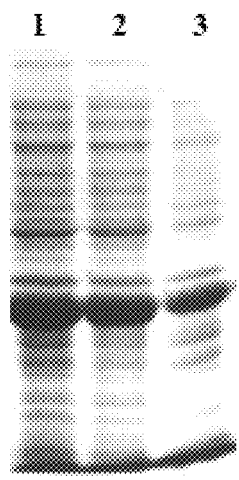
FIG. 1 shows the SDS-PAGE analysis of the recombinant bacteria in which the variant of the annexin V of the embodiment of the present invention expresses. 1: the total bacterial proteins after induced expression; 2: expression supernatant after bacterial broken; 3: expression precipitation after bacterial broken.

Embodiment e: transferring the extracted recombinant expression plasmid into expression host bacteria of *Escherichia coli* BL21(DE3), picking the monoclon to shaking culture at 37° C. overnight, then inoculated in LB culture solution with 1:100 volume, culturing it at 37° C. for 2 hours until $OD_{600}$ is approximately 0.6, adding the inducer IPTG until the final concentration is 0.5 mM, inducing expression at 37° C. for 4 hours, collecting the bacteria, to analysis by using 12% SDS-PAGE. The results of the analysis are shown in FIG. 1, wherein, 1: the total bacterial proteins after induced expression; 2: expression supernatant after bacterial broken; 3: expression precipitation after bacterial broken. The expression level of the variant of the annexin V accounted for 35.4% of the total bacterial proteins, and the vast majority is the soluble form.

Embodiment f: transferring the plasmid pET28a-His-FADD and pET28a-His-FADD (F25Y) into the host strain *E. coli* BL21 (DE3) to expression, and the strain grows on LB agar plates containing kanamycin 37° C. for 16 hours, then picking the monoclon to inoculate into the fresh LB liquid medium (containing 50 mg/L kanamycin), to shaking culture at 37° C. on shaking table, until the $OD_{600}$ of culture fluid is about 0.6; the temperature of shaking table drops to 25° C. and continue to culturing for half an hour, and adding IPTG until which final concentration is 0.4 mM to induce the expression of target protein. After the shaking culture at 25° C. for 5 hours, the bacteria are collected.

Figure 2:
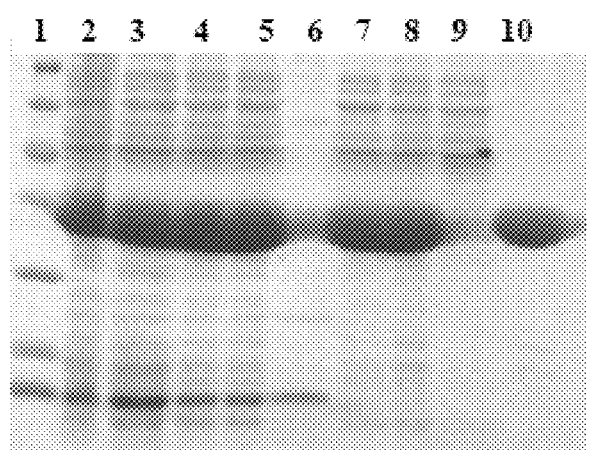
FIG. 2 shows the SDS-PAGE analysis of separation and purification process of the variant of the annexin V of embodiment of the present invention. 1: molecular weight standard substances (from top to bottom are as follows: 116.0, 66.2, 45.0, 35.0, 25.0, 18.4, 14.4 kDa); 2: products of desorption; 3,4: products of ammonium sulfate grated precipitation; 5: purified samples of Super Q-650M chromatography; 6: the peak went through the column of Super Q-650M chromatography; 7: elution peaks of Super Q-650M chromatography; 8: purified samples by SP chromatography; 9: the peak went through the column of SP chromatography; 10: eluting peaks of SP chromatography.

Embodiment g: the bacteria liquid collected in step f, is resuspended with the proportion of 5 mL buffer (50 mM $NH_4Cl$, pH 9.0) to 1 g wet bacteria, and adding lysozyme to treat the bacterial, adding sucrose until concentration is 60% after 1 hour; then diluting it in the buffer (50 mM $NH_4Cl$, 20 mM $CaCl_2$, pH 9.0) with 20 times volume, centrifuging and discarding the supernatant, collecting the precipitate. Resuspending the precipitate with the proportion of 5 mL desorption solution (50 mM $NH_4Cl$, pH 9.0, 20 mM EDTA) to 1 g precipitate, centrifuging and acquiring the supernatant. The supernatant obtained above is grated precipitated by ammonium sulfate, and collecting 40%-70% parts of the precipitation to being re-dissolved and dialysis, then is filtrated to remove insoluble substance. Using starting buffer (50 mM $NH_4Cl$, pH 9.0) to equilibrate the Super Q-650M chromatography column (Japan TOSOH company), using the elution buffer (50 mM $NH_4Cl$, pH 9.0, 200 mM NaCl) to elute, collecting elution peak; using starting 1 buffer (20 mM $NH_4Cl$, 80 mM NaCl, 15 mM $CaCl_2$, pH 9.0) to equilibrate SP chromatography column, and using the elution buffer (20 mM $NH_4Cl$, 400 mM NaCl, pH 9.0) to elute, and collecting the elution peak. analysis The collected fluids are analyzed by SDS-PAGE, and the results are shown in FIG. 2, wherein, 1: molecular weight standard substances (from top to bottom are: 116.0, 66.2, 45.0, 35.0, 25.0, 18.4, 14.4 kDa); 2: products of desorption; 3, 4: products of ammonium sulfate fractionation precipitation; 5: purified samples of Super Q-650M chromatography; 6: the peaks go through the column of Super Q-650M chromatography; 7: elution peaks of Super Q-650M chromatography; 8: purified samples of SP chromatography; 9: the peaks go through the column of SP chromatography; 10: eluting peaks of SP chromatography.

By the above-mentioned purification methods the variant of the annexin V which purity is over 97% is obtained, and more than 110 mg variant of the annexin V is obtained form per liter of fermentation. Through these two highly complementary purification methods of the Super Q column and SP column, most of the hybrid protein can be removed from the variant of the Annexin V. The experimental results also show that: after the two purifications, the purity of protein is over 97%.

Embodiment h: FITC fluorescence labeling of annexin V and the variant of the annexin V: Putting the solution containing 3 mg annexin V and variant of the annexin V into ultra-filtration tube whose molecular weight cut off is 10 KDa, using the 0.1M sodium bicarbonate solution which pH value is 9.0 to conduct ultrafiltration, centrifugation, pouring the supernatant, adding the sodium bicarbonate solution again, repeating that for three times, and measuring the protein concentration. The final concentration is about 5 mg/ml. 200 μl of the solution is taken out and placed in cryule vial before reaction, stirring.

Dissolving 2 mg FITC in 1 ml 0.1M sodium bicarbonate (pH 9.0), stirring rapidly at room temperature. A appropriate amount of FITC solution (molar ratio of FITC and protein is 60 to 100:1) is taken out, and slowly dropped into the protein solution, and controlling the final volume of reaction not exceed 250 μl. The mixture is stirred for two hours at the room temperature in darkness. Using ultrafiltration tube to ultrafiltrate the reaction liquid using PBS (pH 7.2) until the pale green FITC molecules cannot be found in the filtrate, and the products should be yellow-orange transparent solution. The resulting conjugate is packaged with aluminum foil and placed in −20° C. refrigerator.

Figure 3:
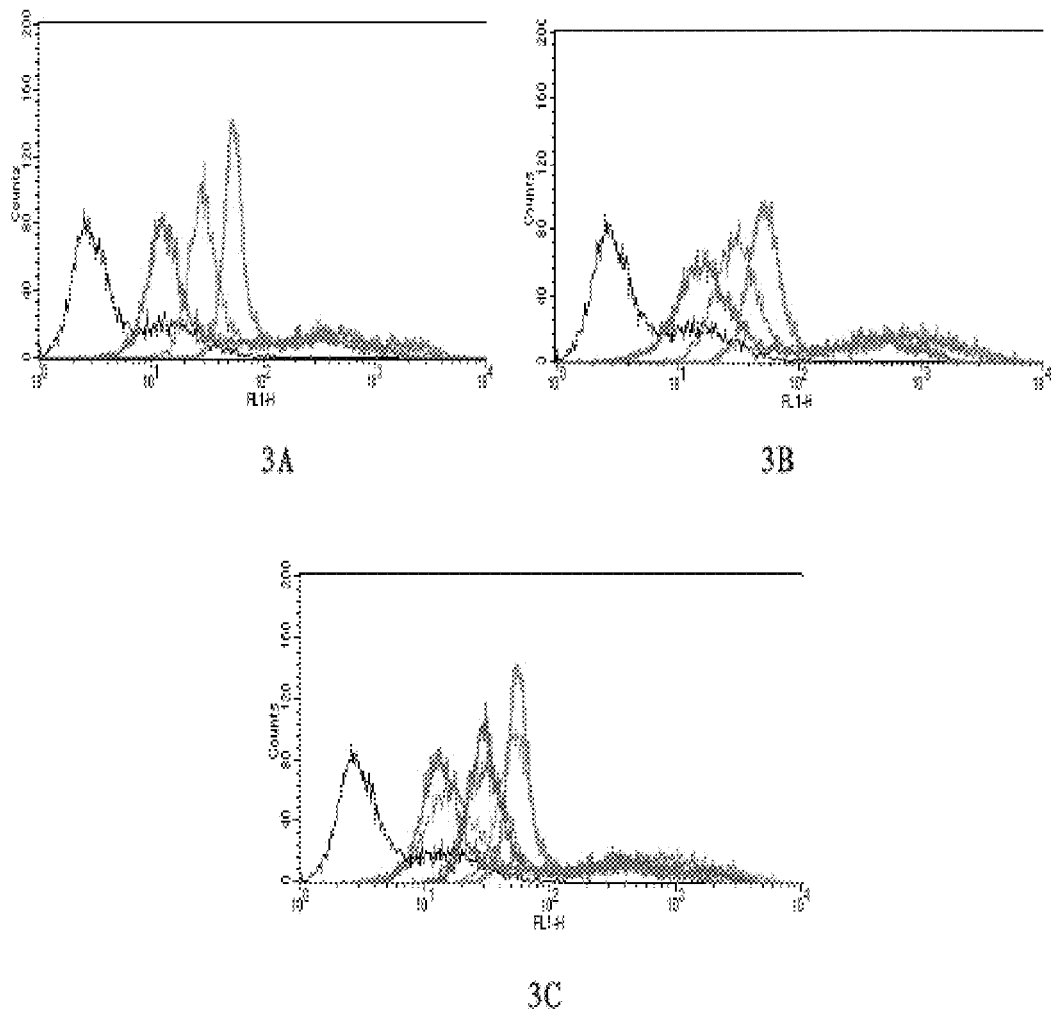
FIG. 3 shows the comparison of the biological activity of the recombinant variant of the annexin V variant and recombinant annexin V of embodiment of the present invention for detecting cell's apoptosis. 3A: different concentrations (green: 0.36 nM; pink: 0.12 nM; Blue: 0.036 nM) of recombinant variants annexin V to detect cell's apoptosis; 3B: different concentration (green: 0.36 nM; pink: 0.12 nM; blue: 0.036 nM) recombinant annexin V and recombinant variants of the annexin V to detect cell's apoptosis; 3C: comparison of the biological activity of different concentrations of the recombinant annexin V and the recombinant variant annexin V for detect cell's apoptosis (green: 0.36 nM; pink: 0.12 nM; blue: 0.036 nM). When the color is same, the probe repressed by the highest peak is FITC-variant of the annexin V.

Embodiment i: comparison of the biological activity for detecting cell's apoptosis of the recombinant variant of the annexin V and the recombinant annexin V: Human lung carcinoma cell A549 (1.5×10$^5$) were treated by 100 ng/ml final concentration of recombinant human TRAIL for 6 hours, digested with trypsin enzyme and centrifuged for 5 minutes to collect the cells at 4° C. and 800 rpm. 400 μl recombinant annexin V or variant of the annexin V containing 0.36 nM, 0.12 nM, 0.036 nM FITC labeled is added into each sample respectively, to detect the cell's apoptosis by flow cytometry. The experiments of each concentration of recombinant annexin V or variant of the annexin V are repeated for three times, with the samples cells without label as a control. The results of the comparation of the biological activity are shown in FIG. 3, wherein, 3A: different concentrations (green: 0.36 nM; pink: 0.12 nM; Blue: 0.036 nM) of recombinant variant of the annexin V to detect cell's apoptosis; 3B: different concentration (green: 0.36 nM; pink: 0.12 nM; blue: 0.036 nM) of recombinant variant of the annexin V to detect cell's apoptosis; 3C: comparison of the biological activity of different concentrations of recombinant annexin V and recombinant variant of the annexin V to detect cell apoptosis (green: 0.36 nM; pink: 0.12 nM; blue: 0.036 nM). For the same color, the probe repressed by the high peak is FITC-variant of the annexin V.

Embodiment j: Radionuclide labeling of the annexin V and the variant annexin V: Dissolving 3.5 mg SnCl$_2$ in 10 ml PBS buffer which pH value is 7.4 to get 0.35 μg/ml SnCl$_2$ solution to be used. Taking 100 μl (35 μg) SnCl$_2$ at room temperature, and adding 20 μl of 0.6 μg/μl annexin V and variant of the annexin V, joggling for 5 minutes. Into it, $^{99}$Tc$^m$O$_4$-solution with the volume less than 0.1 ml and the radiological about 5 mci is added, and then dropping 10 μl Vc and stilling for 30 min at room temperature. The radiochemical purity, which value should be more than 95% for use, of the labeled proteins is detected by HPLC.

Embodiment k: Determination of the stability in vitro of the recombinant variant of the annexin V and the recombinant annexin V labeled by radionuclide: $^{99m}$Tc-annexin V, $^{99m}$Tc-variant of the annexin V stills for 1 hour, 2 hours, 3 hours at room temperature respectively, and then exterminating the radiochemical purity. In addition, when $^{99m}$Tc-annexin V stills for 3 hours, the specific radioactivity is 95%, when stills for 24 hours, the specific radioactivity is 65%; however, when $^{99m}$Tc-variant of the annexin V stills for 3 hours, the specific radioactivity is 98%, when stills for 24 hours, the specific radioactivity also more than 90%. Therefore, the radionuclide labeling of the variant of the annexin V has better stability. $^{99m}$Tc-annexin V and $^{99m}$Tc-variant of the annexin V labeled by radionuclide were injected into animals, and all of them exhibited the same tissue distribution and metabolic characteristics and therefore they all can be used for detection by imaging in vivo.

The specific above-mentioned embodiments illustrate the purpose, technical scheme and beneficial effects of the present invention, however, it will be apparent that they are only the specific examples of the present invention without limitation to the present invention, and various variation, equivalents, modifications etc. without departing from the spirit or principle of the invention will be contained in the scope of the present invention.

What is claimed is:

1. A variant of the annexin V, comprising the amino acid sequence of SEQ ID NO:1, or a protein derived from the variant by one or several amino acid residues being substituted, missing or being added, where the protein derived from the variant has the same activity as the variant;
   wherein the variant or the protein derived from the variant further comprises a short peptide with flexible structure and without branched chain amino acids at the C-terminus of the variant or the protein derived from the variant, wherein the short peptide has 1-25 amino acid residues and contains 1-3 cysteines.

2. The variant of annexin V according claim 1, characterized in that a cysteine is at the C-terminus of the variant.

3. A preparation method of the variant of the annexin V of claim 1, characterized in that: the preparation is carried out as the following steps:
   a. on the basis of the crystal structure of the annexin V, molecular modeling and design of the amino acid sequence for being added to the C-terminus of the annexin V is carried out with the help of the computer-aided molecular design;
   b. designing a pair of primers of the encoding sequence of the annexin V protein, conducting the PCR amplification with the annexin V gene as a template;
   c. connecting the recycled product by the PCR electrophoresis to the cloning vector, and transferring it into the competent *Escherichia coli* cell Top10, and conducting culture;
   d. the recycled product of the step c and expression vector pET28a are digested separately by restriction enzymes of Nco I and Xho I, and the two obtained objective gene fragments are connected by T4 DNA ligase, and transferring it into the competent *Escherichia coli* cell Top10 and conducting the culture and screening to extract the recombinant expression plasmid;
   e. transferring the extracted recombinant expression plasmid into the expression host bacteria of the *Escherichia coli*, culturing the strain to get the bacteria liquid, inducing the bacteria liquid with IPTG, collecting the strain;
   f. expanded culturing the strain_ obtained in step e, collecting the bacteria;
   g. crushing, cracking, purifying the bacteria, to collect the purified protein.

4. A preparation method of the variant of the annexin V according to claim 3, characterized in that: the nucleotide sequences of the pair of the primers are:

```
the sense primer:
5'-gtt cca tgg gcg cac agg ttc tca gag gca-3';

the anti-sense primer:
5'-tcc gct cga gtt agc agt cat ctt ctc cac aga
gca-3'.
```

5. A preparation method of the variant of the annexin V according to claim 3, characterized in that: the purifying step in step g contains successively the precipitation to the desorption, the ammonium sulfate grated precipitation, the column chromatography by Super Q-650M and the column chromatography by SP.

6. A preparation method of the variant of the annexin V as the detection probe of cell apoptosis according to claim 3, characterized in that: it is fluorescence chemically labeled or nuclide labeled.

7. An application of the variant of the annexin V of claim 1 as the detection probe for cell apoptosis, characterized in that: the variant is use in preparing of the monitoring reagents of cell apoptosis, monitoring drugs of disease.

* * * * *

SEQUENCE LISTING

<160> NUMBER OF SEQ ID NOS: 1

<210> SEQ ID NO 1
<211> LENGTH: 346
<212> TYPE: PRT
<213> ORGANISM: Unknown
<220> FEATURE:
<223> OTHER INFORMATION: annexin

<400> SEQUENCE: 1

```
Met Gly Ala Gln Val Leu Arg Gly Thr Val Thr Asp Phe Pro Gly Phe
1               5                   10                  15

Asp Glu Arg Ala Asp Ala Glu Thr Leu Arg Lys Ala Met Lys Gly Leu
            20                  25                  30

Gly Thr Asp Glu Glu Ser Ile Leu Thr Leu Leu Thr Ser Arg Ser Asn
        35                  40                  45

Ala Gln Arg Gln Glu Ile Ser Ala Ala Phe Lys Thr Leu Phe Gly Arg
    50                  55                  60

Asp Leu Leu Asp Asp Leu Lys Ser Glu Leu Thr Gly Lys Phe Glu Lys
65                  70                  75                  80

Leu Ile Val Ala Leu Met Lys Pro Ser Arg Leu Tyr Asp Ala Tyr Glu
                85                  90                  95

Leu Lys His Ala Leu Lys Gly Ala Gly Thr Asn Glu Lys Val Leu Thr
            100                 105                 110

Glu Ile Ile Ala Ser Arg Thr Pro Glu Glu Leu Arg Ala Ile Lys Gln
        115                 120                 125

Val Tyr Glu Glu Glu Tyr Gly Ser Ser Leu Glu Asp Asp Val Val Gly
    130                 135                 140

Asp Thr Ser Gly Tyr Tyr Gln Arg Met Leu Val Val Leu Leu Gln Ala
145                 150                 155                 160
```

-continued

```
Asn Arg Asp Pro Asp Ala Gly Ile Asp Glu Ala Gln Val Glu Gln Asp
            165                 170                 175

Ala Gln Ala Leu Phe Gln Ala Gly Glu Leu Lys Trp Gly Thr Asp Glu
            180                 185                 190

Glu Lys Phe Ile Thr Ile Phe Gly Thr Arg Ser Val Ser His Leu Arg
            195                 200                 205

Lys Val Phe Asp Lys Tyr Met Thr Ile Ser Gly Phe Gln Ile Glu Glu
            210                 215                 220

Thr Ile Asp Arg Glu Thr Ser Gly Asn Leu Glu Gln Leu Leu Leu Ala
225                 230                 235                 240

Val Val Lys Ser Ile Arg Ser Ile Pro Ala Tyr Leu Ala Glu Thr Leu
            245                 250                 255

Tyr Tyr Ala Met Lys Gly Ala Gly Thr Asp Asp His Thr Leu Ile Arg
            260                 265                 270

Val Met Val Ser Arg Ser Glu Ile Asp Leu Phe Asn Ile Arg Lys Glu
            275                 280                 285

Phe Arg Lys Asn Phe Ala Thr Ser Leu Tyr Ser Met Ile Lys Gly Asp
            290                 295                 300

Thr Ser Gly Asp Tyr Lys Lys Ala Leu Leu Leu Leu Cys Gly Glu Asp
305                 310                 315                 320

Asp Gly Ala Gly Gly Ser Ser Gly Gly Cys Ala Gly Gly Ser Ser Gly
            325                 330                 335

Gly Cys Ala Gly Gly Ser Ser Gly Gly Cys
            340                 345
```